US 6,534,455 B1

United States Patent
Maurin et al.

(10) Patent No.: US 6,534,455 B1
(45) Date of Patent: Mar. 18, 2003

(54) COMPOSITION FOR WASHING KERATIN MATERIALS, BASED ON A DETERGENT SURFACTANT, A DIALKYLDIALLYLAMMONIUM HOMOPOLYMER AND AN ACRYLIC TERPOLYMER

(75) Inventors: Véronique Maurin, Paris (FR); Bernard Beauquey, Clichy (FR)

(73) Assignee: L'Oreal, Paris (FR)

( * ) Notice: Subject to any disclaimer, the term of this patent is extended or adjusted under 35 U.S.C. 154(b) by 57 days.

(21) Appl. No.: 09/671,189

(22) Filed: Sep. 28, 2000

(30) Foreign Application Priority Data

Sep. 29, 1999 (FR) .............................. 99 12167

(51) Int. Cl.[7] .............................. C11D 1/04; C11D 1/94; C11D 1/62; C11D 3/26
(52) U.S. Cl. ..................... 510/124; 510/123; 510/125; 510/127; 510/130; 510/158; 510/159; 510/499; 510/504; 510/505; 510/475; 424/70.16; 424/70.17; 424/70.22; 424/70.28; 424/70.31
(58) Field of Search .................. 510/123, 124, 510/125, 127, 130, 158, 159, 499, 504, 505, 475; 424/70.16, 70.17, 70.22, 70.28, 70.31

(56) References Cited

U.S. PATENT DOCUMENTS

| 4,240,450 A | | 12/1980 | Grollier et al. ............... 132/7 |
|---|---|---|---|
| 5,609,862 A | * | 3/1997 | Chen et al. ............... 424/70.11 |
| 6,022,836 A | * | 2/2000 | Dubief et al. ............... 510/122 |
| 6,025,431 A | * | 2/2000 | Cardinali et al. ........... 524/547 |
| 6,372,203 B1 | * | 4/2002 | Allwohn et al. ......... 424/70.13 |

FOREIGN PATENT DOCUMENTS

| DE | 195 40 853 | | 5/1997 |
|---|---|---|---|
| EP | 0 756 860 | | 2/1997 |
| EP | 824914 | * | 2/1998 |
| EP | 0 966 947 | | 12/1999 |
| FR | 2 749 506 | | 12/1997 |
| WO | 94/06403 | | 3/1994 |

* cited by examiner

*Primary Examiner*—Gregory Delcotto
(74) *Attorney, Agent, or Firm*—Jacobson Holman PLLC

(57) ABSTRACT

A composition for washing keratin materials combines in a cosmetically acceptable medium:
  i) at least one detergent surfactant;
  ii) at least dialkyldiallylammonium; and
  iii) at least one acrylic terpolymer made from a monomer (a) chosen from a $C_1$–$C_6$ alkyl acrylate and a $C_1$–$C_6$ alkyl methacrylate; of a monomer (b) chosen from a heterocyclic vinyl compound containing at least one nitrogen or sulphur atom, a (meth)acrylamide, a mono- or di($C_1$–$C_4$)alkylamino($C_1$–$C_4$)alkyl (meth)acrylate and a mono- or di($C_1$–$C_4$)alkylamino($C_1$–$C_4$)alkyl-(meth)acrylamide; of a monomer (c) chosen from a urethane produced by reaction between a monoethylenic unsaturated isocyanate and a nonionic surfactant, a copolymerizable ethylenic surfactant monomer, a surfactant monomer of urea type, an allyl ether containing alkylenoxy groups and a nonionic monomer of urethane type.

41 Claims, No Drawings

COMPOSITION FOR WASHING KERATIN MATERIALS, BASED ON A DETERGENT SURFACTANT, A DIALKYLDIALLYLAMMONIUM HOMOPOLYMER AND AN ACRYLIC TERPOLYMER

Composition for washing keratin materials, based on a detergent surfactant, a dialkyldiallylammonium homopolymer and an acrylic terpolymer The present invention relates in general to compositions for washing keratin materials, based on a detergent surfactant, a dialkyldiallylammonium homopolymer and an acrylic terpolymer, as well as to a washing process using these compositions.

Dialkyldiallylammonium homopolymers are often used in shampoo compositions to improve the cosmetic properties of sensitized hair, for example to make it less coarse and/or to improve its ability to disentangle.

However, it has been found that these dialkyldiallylammonium homopolymers often have the drawback of reducing the cosmetic performance qualities of natural hair, in particular by making them lank.

There is thus a need to develop a detergent cosmetic composition, in particular a shampoo, which gives acceptable cosmetic performance qualities on keratin materials, i.e. in particular the hair and the scalp, and more particularly on natural hair.

The Applicant has discovered, surprisingly, that it is possible to formulate compositions for washing keratin materials, in particular shampoos, having the desired properties, by using in these compositions a detergent surfactant and a dialkyldiallylammonium homopolymer combined with a specific acrylic terpolymer, defined below. Specifically, it has been found that the use of the said acrylic terpolymer in the compositions of the present invention improves the cosmetic properties of keratin materials and in particular natural hair, particularly by making dried natural hair easier to disentangle, smoother, softer, more supple and more manageable. It has also been found that the compositions of the invention give dried hair which looks smoother.

A subject of the invention is thus compositions for washing keratin materials, essentially characterized in that they comprise, in a cosmetically acceptable medium:
i) at least one detergent surfactant;
ii) at least one dialkyldiallylammonium homopolymer; and
iii) at least one acrylic terpolymer consisting of:
   from 5% to 80% by weight, preferably from 15% to 70% by weight and more preferably from 40% to 70% by weight, of an acrylate monomer (a) chosen from a $C_1$–$C_6$ alkyl acrylate and a $C_1$–$C_6$ alkyl methacrylate;
   from 5% to 80% by weight, preferably from 10% to 70% by weight and more preferably from 20% to 60% by weight, of a monomer (b) chosen from a heterocyclic vinyl compound containing at least one nitrogen or sulphur atom, a (meth)acrylamide, a mono- or di($C_1$–$C_4$)alkylamino($C_1$–$C_4$)alkyl (meth)acrylate and a mono- or di($C_1$–$C_4$)alkylamino($C_1$–$C_4$)alkyl(meth)acrylamide;
   from 0.1% to 30% by weight, preferably from 0.1% to 10% by weight, of a monomer (c) chosen from: a urethane produced by reaction between a monoethylenic unsaturated isocyanate and a nonionic surfactant encompassing a block copolymer of 1,2-butylene oxide and of ethylene oxide containing a $C_{1-4}$ alkoxy end;
   a copolymerizable ethylenic unsaturated surfactant monomer obtained by condensing a nonionic surfactant with an α,β-ethylenic unsaturated carboxylic acid or its anhydride;
   a surfactant monomer chosen from reaction products such as urea of a monoethylenic unsaturated monoisocyanate with a nonionic surfactant containing an amine function;
   a (meth)allyl ether of formula $CH_2=CR_1CH_2OA_mB_nA_pR_2$ in which $R_1$ denotes a hydrogen atom or a methyl group, A denotes a propylenoxy or butylenoxy group, B denotes ethylenoxy, n is equal to zero or denotes an integer less than or equal to 200 and preferably less than or equal to 100, m and p denote zero or an integer less than n and $R_2$ is a hydrophobic group of at least 8 carbon atoms and preferably of $C_6$–$C_{30}$; and
   a nonionic monomer such as urethane produced by reaction of a monohydric nonionic surfactant with a monoethylenic unsaturated isocyanate;
   the weight percentages of monomers being based on the total weight of the monomers constituting the terpolymer.

In the washing composition of the invention, the acrylic terpolymer is present in a proportion of from 0.01% to 20% by weight of active material (A.M.), preferably 0.1% to 10% by weight, relative to the total weight of the composition.

Preferred acrylate monomers (a) in particular comprise $C_2$–$C_6$ alkyl acrylates. Ethyl acrylate is most particularly preferred.

Examples of preferred monomers (b) which may be mentioned are N,N-dimethylaminoethyl methacrylate (DMAEMA), N,N-diethylaminoethyl acrylate, N,N-diethylaminoethyl methacrylate, N-t-butylaminoethyl acrylate, N-t-butylaminoethyl methacrylate, N,N-dimethylamino-propylacrylamide, N,N-dimethylaminopropylmethacrylamide, N,N-diethylaminopropylacrylamide and N,N-diethylaminopropylmethacrylamide. N,N-Dimethylaminoethyl methacrylate is most particularly preferred.

The preferred monomers (c) are the copolymerizable ethylenic unsaturated surfactant monomers obtained by condensing a nonionic surfactant with an α,β-ethylenic unsaturated carboxylic acid or its anhydride, preferably $C_3$–$C_4$ mono- or dicarboxylic acids or their anhydrides and more particularly acrylic acid, methacrylic acid, crotonic acid, maleic acid, maleic anhydride and most particularly itaconic acid and itaconic anhydride.

The monomers (c) that are particularly preferred correspond to the copolymerizable ethylenic unsaturated surfactant monomers obtained by condensing a nonionic surfactant with itaconic acid. Among the nonionic surfactants which may be mentioned in particular are $C_{10}$–$C_{30}$ fatty alcohols alkoxylated with 2 to 100 mol and preferably from 5 to 50 mol of an alkylene oxide, such as, for example, polyethylene glycol ethers of $C_{10}$–$C_{30}$ fatty alcohols and more particularly the polyethylene glycol ethers of cetyl alcohol which are known as Ceteth in the CTFA dictionary, 7th edition, 1997.

Conventional methods for preparing these acrylic terpolymers are known to those skilled in the art. Such methods include solution polymerization, precipitation polymerization and emulsion polymerization, for example. Terpolymers in accordance with the invention and methods for preparing them are described in particular in patent applications EP-A-0 824 914 and EP-A-0 825 200.

Among these terpolymers, it is preferred in particular to use the <<Structure® Plus>> polymer sold by the company National Starch, which consists of acrylates, amino(meth)acrylates and $C_{10}$–$C_{30}$ alkyl itaconate, polyoxyethylenated with 20 mol of ethylene oxide, in the form of an aqueous dispersion containing 20% A.M.

In addition to these monomers, the terpolymer can contain other monomers which allow the said terpolymer to be crosslinked. These monomers are used in relatively low proportions, of up to 2% by weight relative to the total weight of the monomers used to prepare the terpolymer. Such crosslinking monomers comprise aromatic monomers bearing several vinyl substituents, alicyclic monomers bearing several vinyl substituents, bifunctional esters of phthalic acid, bifunctional esters of methacrylic acid, multifunctional esters of acrylic acid, N-methylenebisacrylamide and aliphatic monomers bearing several vinyl substituents such as dienes, trienes and tetraenes. Crosslinking monomers may be, in particular, divinylbenzenes, trivinylbenzenes, 1,2,4-trivinylcyclohexene, 1,5-hexadiene, 1,5,9-decatriene, 1,9-decadiene, 1,5-heptadiene, diallyl phthalates, ethylene glycol dimethacrylates, polyethylene glycol dimethacrylates, penta- and tetraacrylates, triallyl pentaerythritols, octaallyl sucroses, cycloparaffins, cycloolefins and N-methylenebisacrylamide.

The dialkyldiallylammonium homopolymer is chosen from homopolymers comprising, as chain constituent, units corresponding to the formula:

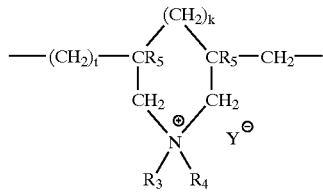

in which formula k and t are equal to 0 or 1, the sum k+t being equal to 1; $R_5$ denotes a hydrogen atom or a methyl radical; $R_3$ and $R_4$, independently of each other, denote an alkyl group containing from 1 to 22 carbon atoms, preferably 1 to 5 carbon atoms, a hydroxyalkyl group in which the alkyl group preferably contains 1 to 5 carbon atoms, a lower amidoalkyl group or $R_3$ and $R_4$ can denote, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate or phosphate. Such polymers are described in particular in French patent 2 080 759 and in its Certificate of Addition 2 190 406.

Among the polymers defined above, mention may be made more particularly of dimethyldiallylammonium chloride homopolymers of different molecular weights and in particular the product sold under the name <<Merquat 100" by the company Merck.

These dialkyldiallylammonium homopolymers may be present in active material concentrations of between 0.01% and 10% by weight, preferably between 0.02% and 8% by weight and even more preferentially in proportions of between 0.05% and 5% by weight, relative to the total weight of the composition.

As mentioned previously, the compositions according to the invention contain at least one detergent surfactant, chosen in particular from anionic, amphoteric, nonionic and cationic surfactants with detergent properties, and mixtures thereof.

Among the anionic surfactants which may be mentioned are alkaline salts, ammonium salts, amine salts, amino alcohol salts and magnesium salts of the following compounds: alkyl sulphates, alkyl ether sulphates, alkylamido ether sulphates, alkylaryl polyether sulphates, monoglyceride sulphates; alkyl sulphonates, alkylamide sulphonates, alkylaryl sulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl phosphates, alkyl ether phosphates; acyl sarcosinates, acyl isethionates, N-acyl taurates.

The alkyl or acyl radical in these various compounds generally consists of a carbon-based chain containing from 8 to 30 carbon atoms.

Among the anionic surfactants which may also be mentioned are fatty acid salts such as oleic, ricinoleic, palmitic and stearic acid salts; coconut oil acid or hydrogenated coconut oil acid; acyl lactylates, in which the acyl radical contains from 8 to 30 carbon atoms.

Surfactants considered as weakly anionic can also be used, such as polyoxyalkylenated carboxylic alkyl or alkylaryl ether acids or salts thereof, polyoxyalkylenated carboxylic alkylamido ether acids or salts thereof, and alkyl D-galactosiduronic acids or salts thereof.

The nonionic surfactants are chosen more particularly from polyethoxylated, polypropoxylated or polyglycerolated fatty acids or alkylphenols or alcohols, with a fatty chain containing 8 to 30 carbon atoms, the number of ethylene oxide or propylene oxide groups being between 2 and 50 and the number of glycerol groups being between 2 and 30.

Mention may also be made of copolymers of ethylene oxide and propylene oxide; condensates of ethylene oxide and of propylene oxide with fatty alcohols; polyethoxylated fatty amides preferably containing 2 to 30 mol of ethylene oxide; polyglycerolated fatty amides preferably comprising 1 to 5 and in particular 1.5 to 4 glycerol groups; polyethoxylated fatty amines preferably containing 2 to 30 mol of ethylene oxide; oxyethylenated fatty acid esters of sorbitan with 2 to 30 mol of ethylene oxide; fatty acid esters of sucrose, fatty acid esters of polyethylene glycol, alkylpolyglycosides, carbamate or amide derivatives of N-alkylglucamines, aldobionamides, amine oxides such as alkylamine oxides or of N-acylamidopropylmorpholine.

The preferred amphoteric surfactants are secondary or tertiary aliphatic amine derivatives, in which the aliphatic radical is a linear or branched chain containing 8 to 22 carbon atoms and which contains at least one carboxylate, sulphonate, sulphate, phosphate or phosphonate water-solubilizing anionic group; ($C_8$–$C_{20}$)alkylbetaines, sulphobetaines, ($C_8$–$C_{20}$)alkylamido ($C_1$–$C_6$) alkylbetaines or ($C_8$–$C_{20}$)alkylamido ($C_1$–$C_6$) alkylsulphobetaines.

Among the amine derivatives which may be mentioned are the products sold under the name Miranol, such as those described in patents U.S. Pat. No. 2,528,378 and 2,781,354 and classified in the CTFA dictionary, 7th edition, 1997, under the name Disodium Cocoamphodiacetate, Disodium Lauroamphodiacetate, Disodium Capryloamphodiacetate, Disodium Caproamphodiacetate, Disodium Cocoamphodipropionate, Disodium Lauroamphodipropionate, Disodium Caproamphodipropionate, Disodium Capryloamphodipropionate, Lauroamphodipropionate acid, Cocoamphodipropionate acid.

The cationic surfactants are chosen in particular from salts of optionally polyoxyalkylenated primary, secondary or tertiary fatty amines; quaternary ammonium salts; imidazoline derivatives; or amine oxides of cationic nature.

The preferred quaternary ammonium salts are tetraalkylammonium halides (for example chlorides) such as, for example, dialkyldimethylammonium chlorides or alkyltrimethylammonium chlroides, in which the alkyl radical contains from about 12 to 22 carbon atoms, in particular behenyltrimethylammonium chloride, distearyldimethylammonium chloride, cetyltrimethylammonium chloride, benzyldimethylstearylammonium chloride or stearamidopropyldimethyl(myristyl acetate)ammonium chloride sold under the name <<Cepharyl 70" by the company Van Dyk.

Diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chlorides or methyl sulphate in particular), and mixtures thereof, can also be used. The acyl radicals preferably contain 14 to 18 carbon atoms and are obtained more particularly from a plant oil such as palm oil or sunflower oil.

The surfactants are used in the compositions in accordance with the invention in proportions that are sufficient to give the composition a detergent nature, generally in a proportion of at least 4% by weight, preferably between 5% and 50% by weight, relative to the total weight of the composition and in particular between 8% and 35%.

The compositions according to the invention have a pH generally of between 3 and 12 and more particularly between 4 and 8.

The cosmetically acceptable medium for the compositions consists either of water or of one or more solvents or of a mixture of water and at least one cosmetically acceptable solvent chosen from lower alcohols, alkylene glycols and polyol ethers.

In one preferred embodiment of the invention, the compositions according to the present invention contain modified or unmodified polyorganosiloxanes, i.e. polyorganosiloxane oils or polyorganosiloxane gums or resins, in their native form or in the form of solutions in organic solvents or alternatively in the form of emulsions or microemulsions.

Among the polyorganosiloxanes which can be used in accordance with the present invention, mention may be made, in a non-limiting manner, of:

I. Volatile silicones: these have a boiling point of between 60° C. and 260° C. They are chosen from cyclic silicones containing from 3 to 7 and preferably 4 to 5 silicon atoms. Examples of these silicones are octamethylcyclotetrasiloxane sold under the name <<Volatile Silicone 7207>> by Union Carbide or <<Silbione 70045 V2>> by Rhône Poulenc, decamethylcyclopentasiloxane sold under the name <<Volatile Silicone 7158>> by Union Carbide and <<Silbione 70045 V5>> by Rhône Poulenc, as well as mixtures thereof. Mention is also made of cyclocopolymers of the dimethylsiloxane/methylalkylsiloxane type, such as <<Volatile Silicone FZ3109>> sold by the company Union Carbide, which is a dimethylsiloxane/methyloctylsiloxane cyclocopolymer.

II. Non-volatile silicones: these consist mainly of:
(i) polyalkylsiloxanes; among the polyalkylsiloxanes which may mainly be mentioned are linear polydimethylsiloxanes containing trimethylsilyl end groups, such as, for example, and in a non-limiting manner, the <<Silbione>> oils of the 70047 series sold by Rhône Poulenc, the oil <<47 V 500 000" from Rhône Poulenc or certain <<Viscasil>> products from General Electric or <<Mirasil>> products from Rhône Poulenc and linear polydimethylsiloxanes containing hydroxydimethylsilyl end groups, such as the oils of the series 48 V from Rh8ne Poulenc;
(ii) polyarylsiloxanes;
(iii) polyalkylarylsiloxanes; mention may be made of linear and branched polymethylphenylsiloxanes, polydimethylmethylphenylsiloxanes and polydimethyldiphenylsiloxanes, such as, for example, the oil <<Rhodorsil 763>> from Rhône Poulenc;
(iv) silicone gums; these are polydiorganosiloxanes with a molecular mass of between 200,000 and 1,000,000, which are used alone or as a mixture in a solvent chosen from volatile silicones, polydimethylsiloxane (PDMS) oils, polyphenylmethylsiloxane (PPMS) oils, isoparaffins, methylene chloride, pentane, dodecane, tridecane and tetradecane, or mixtures thereof; they can correspond to the following structures:
polydimethylsiloxane,
poly[(dimethylsiloxane)/(methylvinylsiloxane)],
poly[(dimethylsiloxane)/(diphenylsiloxane)],
poly[(dimethylsiloxane)/(phenylmethylsiloxane)],
poly[(dimethylsiloxane)/(diphenylsiloxane)/(methylvinylsiloxane)]; mention may also be made, by way of example, and in a non-limiting manner, of the following mixtures:

1) mixtures formed from a polydimethylsiloxane hydroxylated at the end of the chain (Dimethiconol according to the CTFA nomenclature) and from a cyclic polydimethylsiloxane (Cyclomethicone according to the CTFA nomenclature), such as the product <<Q2 1401>> sold by the company Dow Corning;

2) mixtures formed from a polydimethylsiloxane gum with a cyclic silicone, such as the product <<SF 1214 Silicone Fluid>> from General Electric, which is an SE 30 gum of MW 500,000 dissolved in <<SF 1202 Silicone Fluid>> (decamethylcyclopentasiloxane);

3) mixtures of two PDMSs of different viscosity, in particular of a PDMS gum and of a PDMS oil, such as the products <<SF 1236>> and <<CF 1241>> from the company General Electric;

(v) silicone resins; preferably crosslinked siloxane systems containing $R_2SiO_{2/2}$, $RSiO_{3/2}$ and $SiO_{4/2}$ units in which R represents a hydrocarbon group containing 1 to 6 carbon atoms or a phenyl group. Among these resins, mention may be made of the product sold under the name <<Dow Corning 593>>;

(vi) organomodified polyorganosiloxanes; i.e. silicones as defined above, comprising in their general structure one or more organofunctional groups directly linked to the siloxane chain or linked via a hydrocarbon-based radical; mention is made, for example, of silicones comprising:
a) polyethylenoxy and/or polypropylenoxy groups optionally comprising alkyl groups, such as the product known as dimethicone copolyol sold by the company Dow Corning under the name <<DC 1248>> and the alkyl (C12) methicone copolyol sold by the company Dow Corning under the name <<Q2 5200>>;
b) (per)fluoro groups, such as trifluoroalkyl groups, such as, for example, those sold by the company General Electric under the name <<FF.150 Fluorosilicone Fluid>>;
c) hydroxyacylamino groups, such as those described in European patent application EP-A-0 342 834 and in particular the silicone sold by the company Dow Corning under the name <<Q2-8413>>;
d) thiol groups, such as in the silicones <<X 2-8360>> from Dow Corning or <<GP 72A>> and <<GP 71>> from Genesee;
e) substituted or unsubstituted amine groups, such as the products sold under the name GP 4 Silicone Fluid and GP 7100 by the company Genesee or the products sold under the names Q2 8220 and Dow Corning 929 or 939 by the company Dow Corning. The substituted amine groups are, in particular, $C_1$–$C_4$ aminoalkyl or amino($C_1$–$C_4$)alkylamino($C_1$–$C_4$)alkyl groups. The silicones known as amodimethicone and trimethylsilylamodimethicone according to the CTFA name (1997) are used more particularly;

f) carboxylate groups, such as the products described in European patent EP 186 507 from Chisso Corporation;

g) hydroxyl groups, polyorganosiloxanes containing a hydroxyalkyl function, which are described in patent application FR-A-2 589 476;

h) alkoxy groups containing at least 12 carbon atoms, such as the product <<Silicone Copolymer F 755>> from SWS Silicones;

i) acyloxyalkyl groups containing at least 12 carbon atoms, such as, for example, the polyorganosiloxanes described in patent application FR-A-2 641 185;

j) quaternary ammonium groups, such as in the product <<Abil K 3270>> from the company Goldschmidt;

k) amphoteric or betaine groups, such as in the product sold by the company Goldschmidt under the name <<Abil B 9950>>;

l) bisulphite groups, such as in the products sold by the company Goldschmidt under the names <<Abil S 201>> and <<Abil S 255>>;

(vii) block copolymers containing a linear polysiloxane-polyalkylene block as repeating unit; the preparation of such block copolymers used in the context of the present invention is described in European patent application EP 0 492 657 A1, the teaching of which is included in the present description by way of reference;

(viii) grafted silicone polymers, containing a non-silicone organic skeleton, consisting of a main organic chain formed from organic monomers containing no silicone, onto which is grafted, inside the said chain as well as, optionally, on at least one of its ends, at least one polysiloxane macromonomer; in particular those chosen more preferably from those described in U.S. Pat. Nos. 4,963,935, 4,728,571 and 4,972,037 and patent applications EP-A-0 412 704, EP-A-0 412 707, EP-A-0 640 105 and WO 95/00578, the teachings of which are included in their entirety into the present description by way of non-limiting references;

(ix) grafted silicone polymers, containing a polysiloxane skeleton grafted with non-silicone organic monomers, comprising a main polysiloxane chain onto which is grafted, within the said chain as well as, optionally, on at least one of its ends, at least one organic macromonomer containing no silicone; examples of such polymers, as well as the particular method for preparing them, are described in particular in patent applications EP-A-0 582 152, WO 93/23009 and WO 95/03776, the teachings of which are included in their entirety into the present description by way of non-limiting references;

(x) or mixtures thereof.

The polyorganosiloxanes preferably used according to the invention are the aminated or non-aminated non-volatile polydimethylsiloxanes.

The polyorganosiloxanes are used in the compositions of the invention in proportions of between 0.01% and 20% by weight and preferably between 0.1% and 10% by weight relative to the total weight of the composition.

The cosmetic performance qualities of the compositions of the invention can also be improved by adding at least one cationic polymer other than the dialkyldiallylammonium homopolymers chosen from all those already known per se, in particular those described in patent application EP-A-0 337 354 and in French patent applications FR-A-2 270 846, 2 383 660, 2 598 611, 2 470 596 and 2 519 863.

The preferred cationic polymers other than dialkyldiallylammonium homopolymers are chosen from those which contain units comprising primary, secondary, tertiary and/or quaternary amine groups which may either form part of the main polymer chain or be borne by a side substituent linked directly thereto.

The cationic polymers used generally have a molecular mass of between 500 and $5 \cdot 10^6$ approximately and preferably between $10^3$ and $3 \cdot 10^6$ approximately.

Among the cationic polymers which may be mentioned more particularly are quaternized proteins (or protein hydrolysates) and polymers of the polyamine, polyaminoamide and polyquaternary ammonium type. These are known products.

The polymers of the polyamine, polyaminoamide or polyquaternary ammonium type which may be used in accordance with the present invention and which may be mentioned in particular are those described in French patents Nos. 2 505 348 and 2 542 997.

The compositions according to the invention can furthermore also contain at least one adjuvant chosen from the adjuvants usually used in cosmetics, such as fragrances, preserving agents, sequestering agents, wetting agents, sugars, plant, animal, mineral or synthetic oils, amphoteric polymers, menthol, nicotinate derivatives, agents for preventing hair loss, antidandruff agents, foam stabilizers, propellants, dyes, screening agents, ceramides, vitamins or provitamins, and acidifying or basifying agents or other well-known cosmetic adjuvants.

In one preferred embodiment of the invention, the compositions according to the invention are used as shampoos for washing the hair.

The process for washing keratin materials consists in applying a composition as defined above to wet or dry keratin materials in amounts that are effective to wash them, this application being followed by rinsing after an optional period of leaving the composition to stand on the keratin materials.

The example which follows is intended to illustrate the invention.

EXAMPLE OF A SHAMPOO

| | |
|---|---|
| Sodium lauryl ether sulphate (2.2 EO) containing 70% A.M. | 16 g |
| Cocoyl betaine as an aqueous 30% solution | 6 g |
| Glycol distearate | 2 g |
| Terpolymer of acrylates/amino (meth) acrylates/($C_{10}$–$C_{30}$) alkyl itaconate containing 20 mol of EO, as an aqueous 20% dispersion sold by the company National Starch under the name <<Structure ® Plus>> | 2.5 g |
| Coconut acid monoisopropanolamide | 2.5 g |
| Dimethyldiallylammonium chloride homopolymer as an aqueous 40% solution, sold under the name Merquat 100 by the company Merck | 0.75 g |
| Preserving agents qs | 100 g |
| Sterilized demineralized water qs | |

The pH is adjusted to 5.5 with citric acid.

After washing with this shampoo, it is found that dried hair disentangles more easily, feels smoother and softer and is supple and manageable. It has a smooth appearance.

What is claimed is:

1. A composition for washing keratin materials, comprising, in a cosmetically acceptable medium, (I) at least one detergent surfactant, (II) at least one dialkyldiallylammonium homopolymer, and (III) at least one acrylic terpolymer containing, in amounts based on the total weight of monomers constituting the terpolymer:

acrylate monomer (a), in an amount of 5% to 80% by weight and selected from the group consisting of a $C_1$–$C_6$ alkyl acrylate and a $C_1$–$C_6$ alkyl methacrylate;

monomer (b), in an amount of 5% to 80% by weight and selected from the group consisting of a heterocyclic vinyl compound containing at least one nitrogen or sulphur atom, a (meth)acrylamide, a mono- and di($C_1$–$C_4$)alkylamino($C_1$–$C_4$)alkyl (meth)acrylate, and a mono- and di($C_1$–$C_4$)alkylamino($C_1$–$C_4$)alkyl(meth)acrylamide; and monomer (c), in an amount of 0.1% to 30% by weight and selected from the group consisting of:
i) a urethane produced by reaction between a monoethylenic unsaturated isocyanate and a nonionic surfactant comprising a block copolymer of 1,2-butylene oxide and of ethylene oxide with a $C_{1-4}$ alkoxy end;
ii) a copolymerizable ethylenic unsaturated surfactant monomer obtained by condensation of a nonionic surfactant with an α,β-ethylenic unsaturated carboxylic acid or its anhydride;
iii) a urea surfactant monomer produced by reacting a monoethylenic unsaturated monoisocyanate with a nonionic surfactant containing an amine function;
iv) a (meth)allyl ether of formula $CH_2=CR_1CH_2OA_mB_nA_pR_2$ in which $R_i$ denotes a hydrogen atom or a methyl group, A denotes a propylenoxy or butylenoxy group, B denotes ethylenoxy, n is equal to zero or denotes an integer less than or equal to 200, m and p denote zero or an integer less than n, and $R_2$ is a hydrophobic group of at least 8 carbon atoms; and
v) a nonionic urethane monomer produced by reacting a monohydric nonionic surfactant with a monoethylenic unsaturated isocyanate.

2. The composition according to claim 1, wherein the terpolymer is present in a proportion of from 0.01% to 20% by weight relative to the total weight of the composition.

3. The composition according to claim 1, herein the acrylate monomer (a) is a $C_2$–$C_6$ alkyl acrylate.

4. The composition according to claim 1, wherein the monomer (b) is N,N-dimethylaminoethyl methacrylate, N,N-diethylaminoethyl acrylate, N,N-diethylaminoethyl methacrylate, N-t-butylaminoethyl acrylate, N-t-butylaminoethyl methacrylate, N,N-dimethylaminopropylacrylamide, N,N-dimethylaminopropylmethacrylamide, N,N-diethylaminopropylacrylamide or N,N-diethylaminopropylmethacrylamide.

5. The composition according to claim 1, wherein the monomer (c) is a copolymerizable ethylenic unsaturated surfactant monomer obtained by condensing a nonionic surfactant with itaconic acid.

6. The composition according to claim 1, wherein the acrylic terpolymer consists of acrylates, amino(meth)acrylates, and $C_{10}$–$C_{30}$ alkyl itaconate, polyoxyethylenated with 20 mol of ethylene oxide.

7. The composition according to claim 1, wherein the acrylic terpolymer further contains a crosslinking monomer.

8. The composition according to claim 1, wherein, the dialkyldiallylammonium homopolymer is chosen from polymers comprising, as chain constituent, units corresponding to the formula

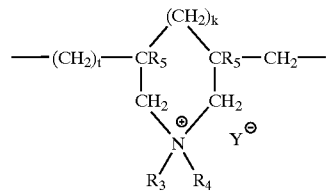

in which k and t are each 0 or 1, the sum k+t being equal to 1; $R_5$ denotes a hydrogen atom or a methyl radical; $R_3$ and $R_4$, independently of each other, denote an alkyl group containing from 1 to 22 carbon atoms, a hydroxyalkyl group in which alkyl contains 1 to 5 carbon atoms, or a lower amidoalkyl group or $R_3$ and $R_4$ denote, together with the nitrogen atom to which they are attached, a heterocyclic group; and $Y^-$ is an anion.

9. The composition according to claim 1, wherein the dialkyldiallylammonium homopolymer is dimethyldiallylammonium chloride homopolymer.

10. The composition according to claim 1, wherein the dialkyldiallylammonium homopolymer is present at a concentration of between 0.01% and 10% by weight relative to the total weight of the composition.

11. The composition according to claim 1, wherein the detergent surfactant is selected from the group consisting of anionic, amphoteric, nonionic, and cationic surfactants and mixtures thereof.

12. The composition according to claim 11, wherein the anionic surfactants are selected from the group consisting of alkaline salts, magnesium salts, ammonium salts, amine salts, and amino alcohol salts of:
alkyl sulphates, alkyl ether sulphates, alkylamido ether sulphates, alkylaryl polyether sulphates, monoglyceride sulphates, alkyl sulphonates, alkylamide sulphonates, alkylaryl sulphonates, olefin sulphonates, paraffin sulphonates, alkyl sulphosuccinates, alkyl ether sulphosuccinates, alkylamide sulphosuccinates, alkyl sulphosuccinamates, alkyl sulphoacetates, alkyl phosphates, alkyl ether phosphates, acyl sarcosinates, acyl isethionates, or N-acyl taurates,
wherein alkyl and acyl is a carbon-based chain containing from 8 to 30 carbon atoms;
fatty acid salts of oleic, ricinoleic, palmitic, or stearic acid; coconut oil acid or hydrogenated coconut oil acid; acyl lactylates, in which the acyl radical contains from 8 to 30 carbon atoms; alkyl D-galactosiduronic acids or salts thereof, polyoxyalkylenated carboxylic alkyl or alkylaryl ether acids or salts thereof, or polyoxyalkylenated carboxylic alkylamido ether acids or salts thereof.

13. The composition according to claim 11, wherein the nonionic surfactants are: polyethoxylated, polypropoxylated, or polyglycerolated fatty acids, alkylphenols, or alcohols having a fatty chain containing 8 to 30 carbon atoms, having between 2 and 50 ethylene oxide or propylene oxide groups, and having 2 and 30 glycerol groups; copolymers of ethylene oxide or of propylene oxide; condensates of ethylene oxide or of propylene oxide with fatty alcohols; polyethoxylated fatty amides; polyglycerolated fatty amides; polyethoxylated fatty amines; oxyethylenated fatty acid esters of sorbitan; fatty acid esters of sucrose or fatty acid esters of polyethylene glycol; alkylpolyglycosides; amide or carbamate derivatives of N-alkylglucamines, aldobionamides, or amine oxides.

14. The composition according to claim 11, wherein the amphoteric surfactants are: secondary or tertiary aliphatic amine derivatives, in which the aliphatic radical is a linear or branched chain containing from 8 to 22 carbon atoms and which contains at least one carboxylate, sulphonate, sulphate, phosphate or phosphonate water-solubilizing anionic group; ($C_8$–$C_{20}$)alkylbetaines, sulphobetaines, ($C_8$–$C_{20}$)alkylamido(C—C)alkylbetaines or (C—C)alkyl-amido($C_1$–$C_6$)alkyl-sulphobetaines.

15. The composition according to claim 11, wherein the cationic surfactants are: optionally polyoxyalkylenated, primary, secondary or tertiary fatty amine salts; quaternary ammonium salts; imidazoline derivatives; or cationic amine oxides.

16. The composition according to claim 1, wherein the detergent surfactant is present in a proportion of at least 4% by weight relative to the total weight of the composition.

17. The composition according to claim 1, having a pH between 3 and 12.

18. The composition according to claim 1, wherein the cosmetically acceptable medium is water, one or more solvents, or of a mixture of water and at least one solvent selected from the group consisting of lower alcohols, alkylene glycols, and polyol ethers.

19. The composition according to claim 1, further comprising at least one volatile or non-volatile silicone selected from the group consisting of:
  i) polyalkylsiloxanes;
  ii) polyarylsiloxanes;
  iii) polyalkylarylsiloxanes;
  iv) silicone gums;
  v) silicone resins;
  vi) organomodified polyorganosiloxanes;
  vii) block copolymers containing a linear polysiloxane-polyalkylene block as a repeating unit;
  viii) grafted silicone polymers, containing a non-silicone organic skeleton;
  ix) grafted silicone polymers, containing a polysiloxane skeleton grafted with non-silicone organic monomers; and
  x) mixtures thereof.

20. The composition according to claim 19, wherein the at least one volatile or non-volatile silicone is present in a proportion between 0.01% and 20% by weight relative to the total weight of the composition.

21. The composition according to claim 1, further comprising at least one cationic polymer selected from the group consisting of:
  quaternized proteins and protein hydrolysates, and
  polyamine, polyaminoamide, and polyquaternary ammonium polymers.

22. The composition according to claim 1, further comprising at least one cosmetically acceptable adjuvant selected from the group consisting of fragrances, preserving agents, sequestering agents, wetting agents, sugars, plant oils, animal oils, synthetic oils, amphoteric polymers, menthol, nicotinate derivatives, agents for preventing hair loss, antidandruff agents, foam stabilizers, propellants, dyes, ceramides, vitamins, provitamins, acidifying agents, and basifying agents.

23. In a shampoo, the improvement wherein the shampoo contains the composition as defined in claim 1.

24. A process for washing keratin materials, comprising the step of applying to the keratin materials, wet or dry, at least one composition as defined in claim 1, and the step of rinsing the keratin materials with water after the applying step.

25. The process according to claim 24, further comprising the step of leaving the composition on the keratin materials for a period of time before the rinsing step.

26. The composition of claim 1, wherein monomer (a) is present in an amount of 15% to 70% by weight.

27. The composition of claim 1, wherein monomer (a) is present in an amount of 40% to 70% by weight.

28. The composition of claim 1, wherein monomer (b) is present in an amount of 10% to 70% by weight.

29. The composition of claim 1, wherein monomer (b) is present in an amount of 20% to 60% by weight.

30. The composition of claim 1, wherein monomer (c) is present in an amount of 0.1% to 10% by weight.

31. The composition of claim 1, wherein $R_2$, in formula $CH_2$=$CR_1CH_2OA_mB_nA_pR_2$, is a hydrocarbon group having 8–30 carbon atoms.

32. The composition of claim 2, wherein the terpolymer is present in a proportion of 0.1% to 10% by weight relative to the total weight of the composition.

33. The composition of claim 3, wherein the monomer (a) is ethyl acrylate.

34. The composition of claim 4, wherein the monomer (b) is N,N-dimethylaminoethyl methacrylate.

35. The composition of claim 8, wherein $R_3$ and $R_4$ are independently an alkyl group containing 1–5 carbon atoms.

36. The composition of claim 8, wherein $Y^-$ is bromide, chloride, acetate, borate, citrate, tartrate, bisulphate, bisulphite, sulfate or phosphate.

37. The composition of claim 10, wherein the concentration is 0.2%–8% by weight.

38. The composition of claim 10, wherein the concentration is 0.5%–5% by weight.

39. The composition of claim 16, wherein the proportion is 5%–50% by weight.

40. The composition of claim 16, wherein the proportion is 8%–35% by weight.

41. The composition of claim 20, wherein the proportion is 0.1%–10% by weight.

* * * * *